(12) United States Patent
Ross

(10) Patent No.: US 10,456,345 B2
(45) Date of Patent: *Oct. 29, 2019

(54) FURTHER PREPARATIONS OF SILK PROTEINS, SEED OILS, MONOSACCHARIDE, NATURAL BOTANICALS AND POLYSACCHARIDE MIXTURES IN COMPOSITIONS FOR HAIR CARE OR HAIR REPAIR, AND SKIN CARE AND TOPICAL TREATMENTS

(71) Applicant: Valerie M. Ross, San Diego, CA (US)

(72) Inventor: Valerie M. Ross, San Diego, CA (US)

(73) Assignee: Valerie M. Ross, San Diego, CA (US)

( * ) Notice: Subject to any disclaimer, the term of this patent is extended or adjusted under 35 U.S.C. 154(b) by 390 days.

This patent is subject to a terminal disclaimer.

(21) Appl. No.: 14/679,977

(22) Filed: Apr. 6, 2015

(65) Prior Publication Data

US 2015/0209261 A1 Jul. 30, 2015

Related U.S. Application Data

(63) Continuation of application No. 13/011,902, filed on Jan. 23, 2011, now Pat. No. 9,023,404.

(60) Provisional application No. 61/412,023, filed on Nov. 10, 2010, provisional application No. 61/297,685, filed on Jan. 22, 2010.

(51) Int. Cl.
| | |
|---|---|
| *A61K 8/64* | (2006.01) |
| *A61K 8/34* | (2006.01) |
| *A61K 8/36* | (2006.01) |
| *A61K 8/44* | (2006.01) |
| *A61K 8/60* | (2006.01) |
| *A61K 8/73* | (2006.01) |
| *A61K 8/97* | (2017.01) |
| *A61Q 5/00* | (2006.01) |
| *A61Q 7/00* | (2006.01) |
| *A61K 9/107* | (2006.01) |
| *A61K 31/715* | (2006.01) |
| *A61K 8/06* | (2006.01) |
| *A61K 36/185* | (2006.01) |
| *A61K 36/55* | (2006.01) |
| *A61K 36/63* | (2006.01) |
| *A61K 36/889* | (2006.01) |
| *A61K 38/17* | (2006.01) |
| *A61K 9/00* | (2006.01) |

(52) U.S. Cl.
CPC ............ *A61K 8/64* (2013.01); *A61K 8/062* (2013.01); *A61K 8/064* (2013.01); *A61K 8/345* (2013.01); *A61K 8/361* (2013.01); *A61K 8/44* (2013.01); *A61K 8/60* (2013.01); *A61K 8/73* (2013.01); *A61K 8/736* (2013.01); *A61K 8/97* (2013.01); *A61K 9/107* (2013.01); *A61K 31/715* (2013.01); *A61K 36/185* (2013.01); *A61K 36/55* (2013.01); *A61K 36/63* (2013.01); *A61K 36/889* (2013.01); *A61K 38/1767* (2013.01); *A61Q 5/002* (2013.01); *A61Q 5/006* (2013.01); *A61Q 7/00* (2013.01); *A61K 9/0014* (2013.01); *A61K 2800/59* (2013.01)

(58) Field of Classification Search
None
See application file for complete search history.

(56) References Cited

U.S. PATENT DOCUMENTS

| | | |
|---|---|---|
| 9,023,404 B2 | 5/2015 | Ross |
| 2005/0002894 A1 | 1/2005 | Petersohn et al. |
| 2008/0274068 A1 | 11/2008 | Tanaka et al. |

FOREIGN PATENT DOCUMENTS

| | | | |
|---|---|---|---|
| JP | 10310530 A | | 11/1998 |
| WO | WO 2009/075383 A1 | * | 6/2009 |

* cited by examiner

*Primary Examiner* — Susan Hoffman
(74) *Attorney, Agent, or Firm* — Edward D. Grieff; Mintz, Levin, Cohn, Ferris, Glovsky and Popeo, P.C.

(57) ABSTRACT

The present invention intends to provide a composition for hair and skin treatment containing a combination consisting of silk amino acid and protein complexes, seed oils, polysaccharides, polyol, monosaccharide, and botanicals. The composition for hair and skin treatment containing the combination consisting of silk amino acid and protein complexes, seed oils, polysaccharides, and botanicals has excellent improvement effects on the condition of the hair follicle and cuticle, imparts moisture to dry hair; thereby reducing the damaging effects of psoriasis, eczema, alopecia, and seborrheic dermatitis. Furthermore, it imparts retention of moisture to the skin resulting in an improved appearance and diminished appearance of lines on the skin. This invention relates to the manufacture of personal care products to be applied to the hair and skin. The compositions may be in the form of hair conditioners, hair growth treatments, shampoos, skin care, skin cleansing, or anti-wrinkle products, and ointments.

15 Claims, No Drawings

FURTHER PREPARATIONS OF SILK PROTEINS, SEED OILS, MONOSACCHARIDE, NATURAL BOTANICALS AND POLYSACCHARIDE MIXTURES IN COMPOSITIONS FOR HAIR CARE OR HAIR REPAIR, AND SKIN CARE AND TOPICAL TREATMENTS

This application is a continuation of Ser. No. 13/011,902, filed Jan. 23, 2011, issued as U.S. Pat. No. 9,023,404, entitled "Further Preparations of Silk Proteins, Seed Oils, Monosaccharide, Natural Botanicals and Polysaccharide Mixtures in Compositions for Hair Care or Hair Repair, and Skin Care and Topical Treatments", which claims the benefit of Provisional Application Nos. 61/412,023, filed Nov. 11, 2010, and 61/297,685, filed Jan. 22, 2010, entitled "Further Preparations of Silk Proteins, Seed Oils, Monosaccharide, Natural Botanicals and Polysaccharide Mixtures in Compositions for Hair Care or Hair Repair, and Skin Care and Topical Treatments", the disclosure of which are incorporated herein by reference in their entirety.

TECHNICAL FIELD AND INDUSTRIAL APPLICABILITY OF INVENTION

The present invention relates to a composition for hair and skin treatment which is characterized by silk amino acid and protein complexes, seed oils, polysaccharides, polyol, monosaccharide, and botanicals.

BACKGROUND ART

The protein structure of the hair is denatured by environmental factors such as uv exposure; physical factors such as heat, friction, and dryness caused by hair dryers, pressing combs, flat-iron straighteners, and so on; and chemical agents such as hair dyes, perms, relaxers, and other hair breaching agents, leading to obstruction of the hair cuticle, decreased water content, degradation of keratin proteins and other constituents of the hair, or the like. The damaged state of the hair leads to splitting of the hair and breaking of the hair, drying out of the hair, decreased elasticity, etc.

The cosmetic industry has traditionally treated these problems using silicones, fats and oils, amino acids, polyols, etc. However, the benefits of standard conventional treatments have shortcomings in scope of treatment and are not beneficial for a broad range of hair and skin conditions.

The present invention contains water-soluble silk protein, which deposits onto the skin or the natural hair keratin to provide a smooth and durable film to provide added strength for protection against environmental, chemical, and grooming associated damage. Furthermore, cationic polysaccharides, including but not limited to chitosan and its corresponding derivatives, bind to human skin and hair and provide damage control by binding to the amino acids comprising the hair when the hair has been damaged by surfactants, dyeing, and perming. The seed oils present in the emulsions provide a moisture barrier and act as carriers of the nutrients into the pores of the hair and skin.

Botanical extracts contain polyphenols, among other actives, which contribute to a wide range of medicinal qualities such as Anti-inflammatory effect, Anti-cancer effect, Potent DHT inhibitor, stimulant, among others. For example, the bark and roots of *Myrica rubra* contain essential oil, triterpenes (taraxerol, myricadiol), gallic tannins and flavonoids (myricetin and dihyidromyricetin). Among them, myricetin is the standardized compound in the extract which is astringent and stimulant, and has anti-inflammatory and anti-cancer effects.

Botanicals, such as *Myrica rubra* extract, rosehip extract, and green tea extract, contain flavonoids which are naturally occurring phenolic compounds, found in plants, that exhibit a variety of biological activities, including suppression of inflammation, cancer chemoprevention, and protection from vascular disease.

Compounds such as organic anthocyanins and other plant pigments are found in the hibiscus, in addition, relatively large amounts of the oxalic, malic, citric-12% to 17%, and tartaric acids are also found. The herb also contains very appreciable quantities of many water soluble mucilaginous polysaccharides in high proportions to the total volume. These water soluble mucilaginous polysaccharides coat and protect the hair and skin.

Furthermore, the combination of amino acids, polyol, D-ribose, polysaccharide, and fatty acids are expected to increase oxygen uptake of the hair follicle with the result of stimulating the metabolic processes of the hair follicle leading to reparation of damaged follicles. While the cationic polysaccharides and the silk proteins bind to the hair thereby controlling damage to the hair.

Both oil/water (O/W) emulsions and water/oil (W/O) emulsion systems have been prepared. O/W systems are formulated for the treatment of dry skin and hair conditions. W/O based systems are formulated for skin and hair which is excessively dry damaged, and porous, which require higher concentration of follicle-penetrating oils.

EXPERIMENTAL DATA

Water/Oil Preparation for Hair Care and Hair Growth Conditioner

Phase A: Olive oil (5-25%), coconut oil (20-40%), Flaxseed oil (5-25%), jojoba oil (5-25%), Sorbitan olivate (1-9%), Sucrose cocoate (0.05-2%), Behenyl alcohol (1-5%), PCA Glyceryl Oleate (0.1-4%), Illipe butter (0.05-6%).

Phase B: Purified water (5%-20%), Citrus pectin (0.001-0.05%), Chitosan (0.003-0.05%), Sodium chloride (0.003%-0.05%), Citric acid (0.1-1%), Hydrolyzed keratin (0.03%-3%), Silk amino acids (0.1%-0.7%), Sericin (0.03%-3%), Aloe vera (0.005%-1%), Glycerine (5-15%), Potassium sorbate (0.04-2%), D-ribose (0.001%-3%), *Myrica rubra* extract (0.003-5%), Sodium PCA (1%-13%), Kelp (0.01-2%), Panthenol (1-5%), Chitosan succinamide (0.1-5%), Sunflower seed extract (0.003-5%), Muira Puama extract (0.003-5%).

Phase C: vitamin e acetate (0.04%-4%), Natural Fragrance (0.05%-3%), Manuka oil (0.05%-3%).

Oil/Water Preparation for Leave-In Hair Care and Hair Growth Conditioner

Phase A: Cucumber Seed extract (0.1-4%), Purified water (50-90%), Citrus pectin (0.001-0.05%), Chitosan (0.003-0.9%), citric acid (0.1-1%), Sericin (0.03%-3%), aloe vera (0.005%-1%), potassium sorbate (0.04-2%), D-ribose (0.001%-3%), *Myrica rubra* extract (0.003%-5%), Kelp (0.01-3%), Panthenol (1-5%), Sorbitol (1-11%), Chitosan succinamide (0.1-5%), Sunflower seed extract (0.003-5%), Muira Puama extract (0.003-5%).

Phase B: Olive oil (5-10%), coconut oil (5-10%), Flaxseed oil (5-10%), jojoba oil (5-10%), Behentrimonium methosulfate (0.05-2%), Behenyl alcohol (0.5-5%), Illipe butter (0.05-6%).

Phase C: vitamin e acetate (0.04%-4%), Natural Fragrance (0.05%-3%), Manuka oil (0.05%-3%).

Oil/Water Preparation for Rinse Out Hair Care and Hair Growth Conditioner for Normal to Dry Hair Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.1%-0.7%), Sericin (0.03%-3%), aloe vera (0.005%-1%), potassium sorbate (0.04-2%), D-ribose (0.001%-3%), *Myrica rubra* extract (0.003%-5%), Sunflower seed extract (0.01-3%), Chamomile flower extract (0.01-3%), Rosmarinus officinalis extract (0.01-3%), Arctium lappa extract (0.01-3%), Quinoa extract (0.01-3%), Panthenol (1-5%), Sorbitol (1-11%), Muira Puama extract (0.003-5%).

Phase B: Sweet almond oil (1-10%), Avocado oil (1-10%), Sucrose cocoate (0.1-5%), Behentrimonium methosulfate (0.05-5%), Behenyl alcohol (0.05-5%).

Phase C: vitamin e acetate (0.04%-4%), Natural Fragrance (0.05%-3%), Manuka oil (0.05%-3%).

Oil/Water Preparation for Rinse Out Hair Care and Hair Growth Conditioner for Dry Hair Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.1%-0.7%), Sericin (0.03%-3%), aloe vera (0.005%-1%), potassium sorbate (0.04-2%), D-ribose (0.001%-3%), *Myrica rubra* extract (0.003%-5%), Sunflower seed extract (0.01-3%), Chamomile flower extract (0.01-3%), Rosmarinus officinalis extract (0.01-3%), Arctium lappa extract (0.01-3%), Quinoa extract (0.01-3%), Panthenol (1-5%), Sorbitol (1-11%), Muira Puama extract (0.003-5%), Chitosan succinamide (0.1-5%).

Phase B: Sweet almond oil (1-10%), Avocado oil (1-10%), Sucrose cocoate (0.1-5%), Behentrimonium methosulfate (0.05-5%), Behenyl alcohol (0.05-5%), Wipe butter (0.05-6%).

Phase C: vitamin e acetate (0.04%-4%), Natural Fragrance (0.05%-3%), Manuka oil (0.05%-3%).

Preparation for Hair Care and Hair Growth Shampoo Low Foam

Phase A: Purified water (50-90%), Cocamidopropyl Hydroxysultaine (5-18%), Sodium Cocoyl Glutamate (3-10%), Yucca schidigera extract (1-10%), Saponaria officinalis (1-10%), Sucrose cocoate (1-10%), Soapwort root extract (1-10%).

Phase B: Camellia oil (1-10%).

Phased C: Honey (1-10%), Citrus pectin (0.001-0.05%), Chitosan (0.003-0.9%), citric acid (0.1-1%), Hydrolyzed keratin (0.03%-5%), silk amino acids (0.1%-0.7%), Sericin (0.03%-3%), potassium sorbate (0.04-2%), Glycerine (5-15%), D-ribose (0.001%-3%), *Myrica rubra* extract (0.003%-5%), Sodium PCA (0.01-5%), Hibiscus flower extract (0.01-3%), Ginger extract (0.01-3%), Green tea extract (0.01-3%), Sandalwood extract (0.01-3%), Rosehip extract (0.01-3%), Ginkbo biloba extract (0.01-3%), Mango extract (0.01-3%), Ashwaganda extract (0.01-3%), Kelp (0.01-3%), Allantoin (0.1-5%), Xanthan gum (0.1-3%), Sodium citrate (0.1-2%), Muira Puama extract (0.003-5%).

Phase D: vitamin e acetate (0.04%-4%), Eucalyptus oil (0.01%-3%), Sage clary oil (0.01-3%), Natural Fragrance (0.05%-3%)

Preparation for Hair Care and Hair Growth Shampoo no Foam

Phase A: Purified water (50-90), Sucrose cocoate (1-15%).

Phase B: Camellia oil (1-10%).

Phased C: Honey (1-10%), Citrus pectin (0.001-0.05%), Chitosan (0.003-0.9%), citric acid (0.1-1%), Hydrolyzed keratin (0.03%-5%), silk amino acids (0.1%-0.7%), Sericin (0.03%-3%), potassium sorbate (0.04-2%), Glycerine (5-15%), D-ribose (0.001%-3%), *Myrica rubra* extract (0.003%-5%), Sodium PCA (0.01-5%), Hibiscus flower extract (0.01-3%), Ginger extract (0.01-3%), Green tea extract (0.01-3%), Sandalwood extract (0.01-3%), Rosehip extract (0.01-3%), Ginkbo biloba extract (0.01-3%), Mango extract (0.01-3%), Ashwaganda extract (0.01-3%), Kelp (0.01-3%), Allantoin (0.1-5%), Xanthan gum (0.1-3%), Sodium citrate (0.1-2%), Muira Puama extract (0.003-5%).

Phase D: vitamin e acetate (0.04%-4%), Eucalyptus oil (0.01%-3%), Sage clary oil (0.01-3%), Natural Fragrance (0.05%-3%)

Preparation for Carrier Oil-Free Smoothing Gel

Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.01%-0.7%), Sericin (0.03%-3%), potassium sorbate (0.04-2%), D-ribose (0.001%-3%), *Myrica rubra* extract (0.003%-5%), Sodium PCA (0.1-2%), Collagen amino acids (0.01-4%), Carob extract (0.01-3%), Grapeseed extract (0.01-3%), Grapefruit seed extract (0.01-3%), Rosmarinus officinalis extract (0.01-3%), Olive seed extract (0.01-3%), Seaweed codium vermilara extract (0.01-3%), Panthenol (1-5%), Sorbitol (1-11%), Polysorbate 60 (0.03-5%), Xanthan gum (0.02-2%).

Phase B: vitamin e acetate (0.01%-4%), Fragrance (0.05%-3%)

Preparation for Carrier Oil Containing Smoothing Gel

Phase A: Honey (1-10%), Purified water (50-90%), Citrus pectin (0.001-0.05%), Chitosan (0.003-0.9%), citric acid (0.1-1%), hydrolyzed keratin (0.03%-5%), silk amino acids (0.01%-0.7%), Sericin (0.03%-3%), potassium sorbate (0.04-2%), D-ribose (0.001%-3%), *Myrica rubra* extract (0.003%-5%), Sodium PCA (0.1-2%), Collagen amino acids (0.01-4%), Carob extract (0.01-3%), Grapeseed extract (0.01-3%), Grapefruit seed extract (0.01-3%), Rosmarinus officinalis extract (0.01-3%), Olive seed extract (0.01-3%), Seaweed codium vermilara extract (0.01-3%), Panthenol (1-5%), Sorbitol (1-11%), Polysorbate 60 (0.03-5%), Xanthan gum (0.02-2%).

Phase B: Plum kernel oil (1%-10%), Behentrimonium methosulfate (0.05-5%), Behenyl alcohol (0.05-5%), PCA Glyceryl Oleate (0.1-4%).

Phase C: vitamin e acetate (0.01%-4%), Fragrance (0.05%-3%)

General Procedure for Preparation of Hair Care and Hair Growth Conditioner and Gels Phase A was prepared in stainless-steel apparatus with agitation at low speed (approx. 200 rpm) and heated to 75 C-80 C. Phase B was prepared similarly with agitation at low speed and heating to 75 C-80 C. Phase A was then agitated at high speed (over 1000 rpm), subsequently Phase B was slowly added to Phase A. High speed agitation was continued for 5 minutes. The mixture was cooled to 45-50 C, then phase C was added to mixture and the mixture was allowed to cool to room temperature with low speed agitation.

General Procedure for Preparation of Hair Care and Hair Growth Shampoo

Phase A was prepared in stainless-steel apparatus with agitation at low speed (approx. 200 rpm) and heated to 75 C-80 C. Phase B followed by Phase C were added with agitation and heating to 75 C-80 C. The mixture was cooled to 45-50 C, then phase D was added to mixture and the mixture was allowed to cool to room temperature with low speed agitation.

General Procedure for Preparation of Hair Care and Hair Growth Smoothing Gel

Phase A was prepared in stainless-steel apparatus with agitation at low speed (approx. 200 rpm) and heated to 75 C-80 C. The mixture was cooled to 45-50 C, then phase B was added to mixture and the mixture was allowed to cool to room temperature with low speed agitation.

Further Applications

The emulsion systems for the W/O are currently composed of, but not limited to suitable monoester of fatty acids derived from olive oil and sorbitol (sorbitan olivate), and monoester of sucrose esters of coconut acids derivatives (sucrose cocoate). Suitable emulsion stabilizer is composed of, but not limited to individual components/or combination of single oleate derivative, PCA glyceryl oleate; propylene glycol ether derivatives of cellulose (hydroxypropyl methylcellulose); and/or long-chain fatty alcohols (behenyl alcohol, cetyl alcohol, stearyl alcohol, or other suitable long-chain fatty alcohols). The W/O emulsifier system may vary within limits. It is preferable to use a combination of nonionic, unsaturated, long-chain fatty acid ester of low hydrophilic/lipophilic balance (HLB) value in combination with a high HLB polyethoxylated fatty acid ester.

These emulsions, which are in the form of creams, oils, gels, have good film-forming properties and give a very satisfactory sensation after they have been applied. Such emulsions can be used as skin care, skin cleansing. When these compositions are skin care products, including but not limited to anti-wrinkle products for improving the appearance of the skin. These can be used as skin care and anti-wrinkle products with the addition of a range of vitamins, including but not limited to vitamin A, B, C sources and derivatives derived thereof (0.05%-5%). Addition of carbohydrates is recommended, preferably, but not limited to the glycosaminoglycan hyaluronic acid (0.01%-2%). Addition of botanical extracts, preferably, but not limited to green tea extracts (0.5%-7%). Addition of exfoliating agents is recommended, preferably, but not limited to avena saliva kernel flour (0.05%-5%).

These emulsions, which are in the form of creams, oils, and gels, based on their ability to promote hair growth, exhibit epidermal penetration properties, and give a very satisfactory sensation after they have been applied. Such emulsions can be used as topical ointments. These compositions may be suitable health care products, including, but not limited topical ointments for the relief of pain. These can be used as topical products with the addition of a range of vitamins, including but not limited to vitamin A, B, C sources and derivatives derived thereof (0.05%-5%). Addition of marine extracts is recommended, preferably, but not limited to kelp (0.05%-5%). Addition of botanical extracts, preferably, but not limited to Ho Shou Wu root extracts (0.005%-3%). Addition of high molecular weight wax is recommended, preferably, but not limited to medical grade lanolin (2%-20%).

The invention claimed is:

1. A topical composition comprising: sericin; chitosan; and ribose; wherein the sericin, chitosan, and ribose are part of a first phase comprising water, and wherein the topical composition comprises a water-in-oil emulsion formed from the first phase and a second phase comprising at least one seed oil.

2. The topical composition of claim 1, further comprising *Myrica rubra* extract in the first phase.

3. The topical composition of claim 2, wherein the *Myrica rubra* extract is present in the first phase in a *Myrica rubra* extract concentration range of approximately 0.003% to 5%.

4. The topical composition of claim 1, wherein the ribose is present in the first phase in a ribose concentration range of approximately 0.001% to 3%.

5. The topical composition of claim 1, wherein the chitosan is present in the first phase in a chitosan concentration range of approximately 0.003% to 0.05%.

6. The topical composition of claim 1, further comprising *quinoa* extract.

7. The topical composition as in claim 1, further comprising kelp extract, sunflower seed extract, cucumber seed extract, grape seed extract, grapefruit seed extract, olive seed extract, or a combination of two or more thereof.

8. The topical composition of claim 1, further comprising flaxseed oil in a flaxseed oil concentration range of approximately 5 to 25%.

9. The topical composition of claim 1, further comprising silk amino acids in a silk amino acid concentration range of approximately 0.1% to 0.7%.

10. The topical composition of claim 1, wherein the sericin is present in a sericin concentration range of approximately 0.03% to 3%.

11. The topical composition of claim 1, wherein the emulsion comprises a nonionic, unsaturated, long-chain fatty acid ester of low hydrophilic/lipophilic balance value in combination with a high hydrophilic/lipophilic balance polyethoxylated fatty acid ester.

12. The composition of claim 1, further comprising olive oil, coconut oil, flaxseed oil, jojoba oil, sorbitan olivate, sucrose cocoate, behenyl alcohol, PCA glyceryl oleate, illipe butter, water, citrus pectin, sodium chloride, citric acid, hydrolyzed keratin, a silk amino acid, aloe vera, glycerin, potassium sorbate, *Myrica rubra* extract, sodium PCA, kelp extract, panthenol, sunflower seed extract, muira puama extract, vitamin E acetate, manuka oil, or a combination of two or more thereof.

13. The composition of claim 1, further comprising olive oil, sorbitan olivate, sucrose cocoate, PCA glyceryl oleate, hydroxypropyl methylcellulose, behenyl alcohol, cetyl alcohol, stearyl alcohol, vitamin A, vitamin B, vitamin C, glycosaminoglycan hyaluronic acid, green tea extract, Avena sativa kernel flour, kelp extract, Ho Shou Wu root extract, lanolin, or a combination of two or more thereof.

14. The composition of claim 1, wherein the topical composition is a cream, an oil, or a gel.

15. A method of treating a hair condition and/or a skin condition in a subject in need thereof, the method comprising administering to the subject an effective amount of the composition of claim 1 where the hair condition and/or skin condition is selected from the group consisting of a denatured protein structure of the hair, a degradation of at least one keratin protein of the hair, an obstruction of a hair cuticle on the skin, a decreased water content of the skin, dandruff, eczema, psoriasis, seborrheic dermatitis, or alopecia.

* * * * *